US00PP37647P2

(12) United States Plant Patent
Hansen

(10) Patent No.: US PP37,647 P2
(45) Date of Patent: Aug. 25, 2026

(54) ***HEUCHERA* PLANT NAMED 'Glazed and Infused'**

(50) Latin Name: ***Heuchera* hybrid**
Varietal Denomination: Glazed and Infused

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 19/729,001

(22) Filed: Jan. 14, 2026

(51) Int. Cl.
*A01H 5/12* (2018.01)
*A01H 6/80* (2018.01)

(52) U.S. Cl.
USPC ..... Plt./440

(58) Field of Classification Search
USPC ..... Plt./263.1, 440
See application file for complete search history.

(56) References Cited

U.S. PATENT DOCUMENTS

PP12,066 P2 * 8/2001 Oliver ..... A01H 5/12 Plt./440
PP24,770 P2 * 8/2014 Leue ..... A01H 6/80 Plt./440

* cited by examiner

*Primary Examiner* — Karen M Redden

(57) ABSTRACT

The new and distinct hybrid of *Heuchera* plant named 'Glazed and Infused' produced large mounds of large, cordate, moderately-dissected, mostly flat leaf blades of charcoal-black surrounding the veins and heavy silver between the veins. The new plant has upright, branched panicles producing deep rose-pink flowers without vernalization. The new plant is vigorous and produces large clumps with many dense leaves and is useful in the landscape or in containers.

2 Drawing Sheets

Botanical denomination: *Heuchera* hybrid.
Variety denomination: 'Glazed and Infused'.

STATEMENT REGARDING PRIOR DISCLOSURES UNDER 37 CFR 1.77(B)(6)

The first offer for sale of *Heuchera* 'Glazed and Infused' was a private offer to In the Country Garden & Gifts by Walters Gardens, Inc. on Jan. 17, 2025, on a website maintained by Walters Gardens, Inc. Subsequently, on Feb. 1, 2021, Walters Gardens, Inc. introduced the new plant on their website and in the "Walters Gardens 2025-2026 Catalog" initially released on Jun. 3, 2025, with a brief description and photograph. No plants of *Heuchera* 'Glazed and Infused' have been sold, in this country or anywhere in the world, nor has any disclosure of the new plant been made more than one year prior the filing date of this application and such sale or disclosure within one year was either derived directly or indirectly from the inventor and would be a 35 USC § 102(b) exception.

BACKGROUND OF THE INVENTION

The present invention relates to a new and distinct cultivar of Coral Bells in the Saxifragaceae family and given the cultivar name of 'Glazed and Infused'. 'Glazed and Infused' was hybridized by the inventor on Sep. 23, 2021, in the greenhouses of a wholesale perennial nursery in Zeeland, Michigan, USA and assigned the breeder code 21-26-25. The seed or female parent was the proprietary, unreleased and unnamed hybrid assigned the breeder code 12-113-6

(not patented); the male parent was the proprietary, unreleased and unnamed hybrid assigned the breeder code 18-10-5 (not patented).

*Heuchera* 'Glazed and Infused' was first selected in the fall of 2022 and passed final evaluation in the fall of 2023 from among thousands of other seedlings from the same cross and other crosses. 'Glazed and Infused' has been asexually propagated by basal shoot cuttings at the same nursery in Zeeland, MI in 2022 and by careful shoot tip tissue culture propagation, and the resultant plants have remained stable and continued to exhibit the same characteristics as the original plant for multiple generations.

BRIEF SUMMARY OF THE INVENTION

*Heuchera* 'Glazed and Infused' differs from its parents as well as all other coral bells known to the applicant in the following combined traits:

1. The large-sized, cordate, leaf blades have moderately dissected lobes;
2. Leaves mostly flat with rounded lobe apices;
3. Foliage has lightly overlapping and indented or folded at major veins;
4. Leaves have heavy silver between the veins and charcoal-black surrounding the veins;
5. Produces large-sized clumps and many individual leaves;
6. Plant habit is vigorous with medium height stems of deep rose-pink flowers.

In comparison to the new plant, the female parent has leaves that are chartreuse with slightly less silvery blush between the veins and the flowers are more reddish on darker wine-color panicles. The male parent is similar in habit and size but the leaves are more coarsely waved, more purplish and less pewter between the veins, and the flowers are smaller and more spread apart on the scapes.

The most similar cultivars known to the inventor are: 'Paris' U.S. Plant Pat. No. 18,881, 'Prom Dress' U.S. Plant Pat. No. 36,610, 'Silver Gumdrop' U.S. Plant Pat. No. 29,207, 'Silver Scrolls' U.S. Plant Pat. No. 12,066, 'Smoke and Mirrors' U.S. Plant Pat. No. 31,785, and 'Timeless Treasure' U.S. Plant Pat. No. 31,987.

'Paris' has a smaller habit and smaller leaves that are green with silver between the veins and the flowers are deep pink aging to dark pink on shorter scapes. 'Prom Dress' has larger flowers on shorter panicles, larger flatter leaves with more ruffling of the foliage, and the top surface is slightly shiny. 'Silver Gumdrop' has a smaller habit and smaller leaves and the foliage color tends to be lighter and more greenish. 'Silver Scrolls' has smaller leaves with lighter less charcoal-black color surrounding the veins and more greenish and purplish undertone. 'Smoke and Mirrors' has smaller slightly shinny leaves with strong purplish undertones in spring and become silver with deep green surrounding the veins in summer and the calyces are deeper reddish colored. 'Timeless Treasure' has smaller leaves with less silver, and larger darker reddish flowers on shorter panicles over a longer season.

BRIEF DESCRIPTION OF THE DRAWINGS

The photographs of the new plant demonstrate the overall appearance of *Heuchera* 'Glazed and Infused' including the unique traits. The colors are as accurate as reasonably possible with modern color reproductions. Some slight variation of color may occur as a result of lighting quality, intensity, wavelength, and direction or reflection.

DETAILED BOTANICAL DESCRIPTION

Figure 1:
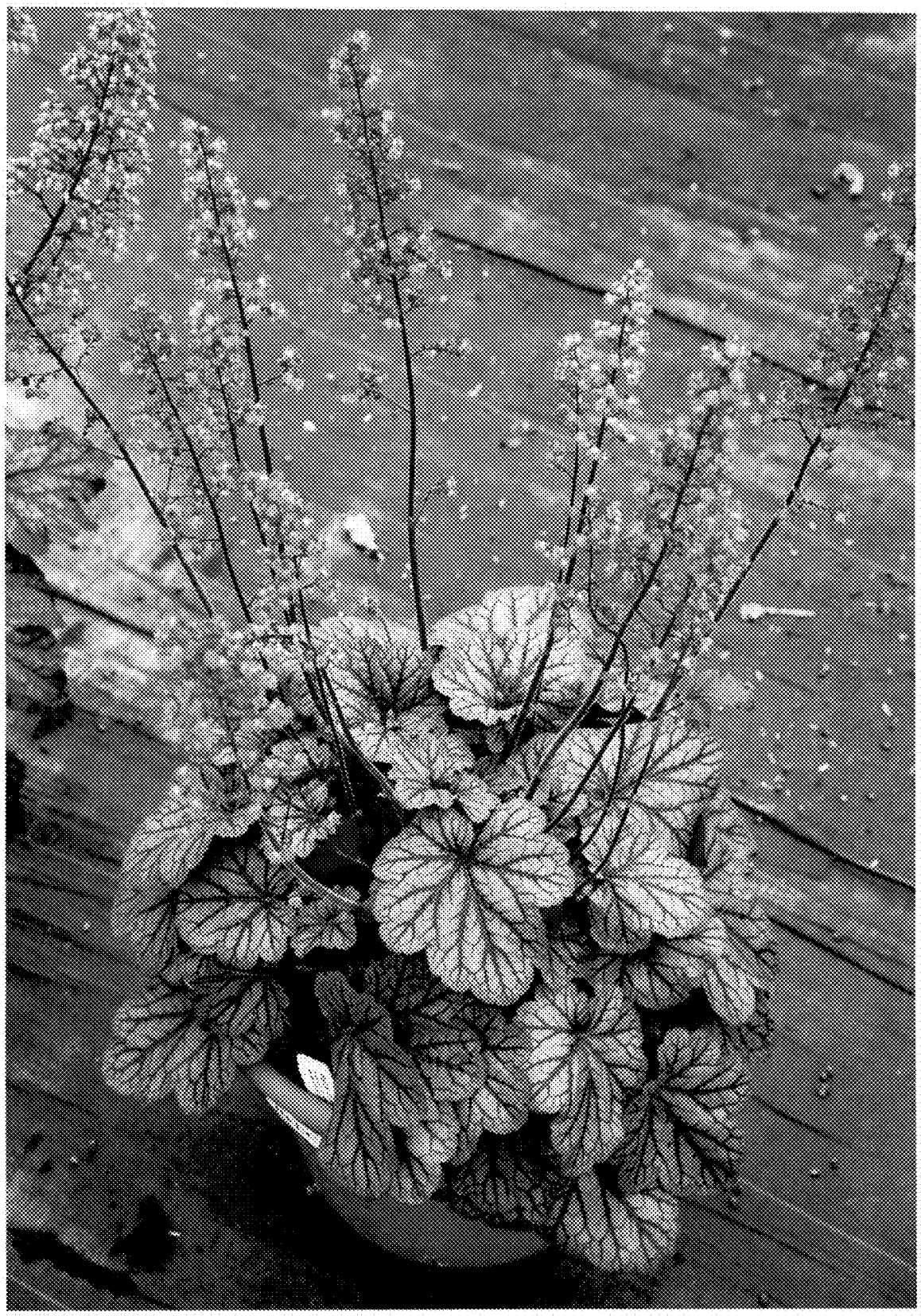
FIG. 1 shows a two-year-old plant late in the season.
Figure 2:
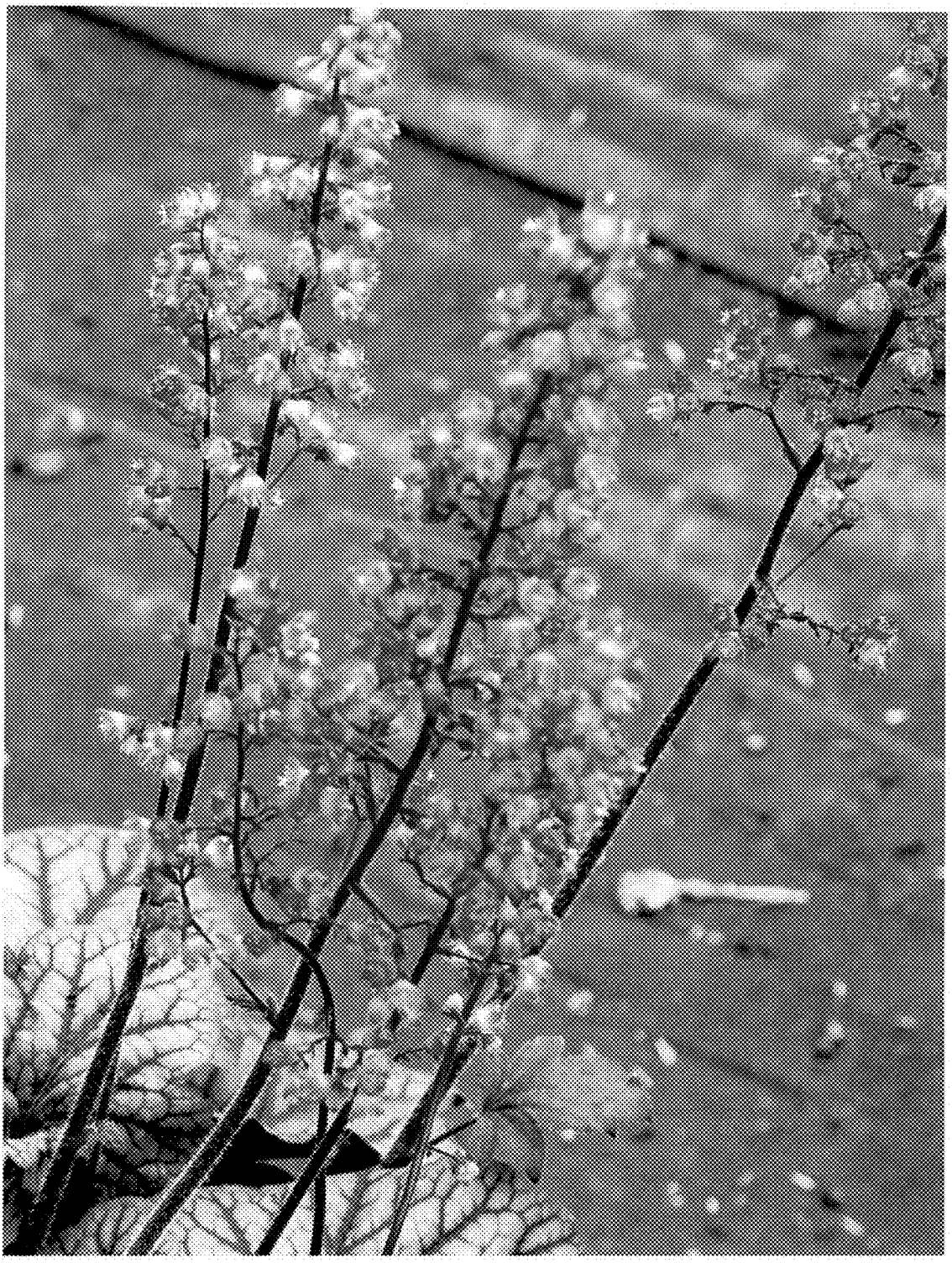
FIG. 2 shows the scapes with flowers and buds.

The following description is based on a three-year-old plant growing in a lightly shaded greenhouse in Zeeland, Michigan, USA. The new plant has not been grown under all possible environments and may phenotypically appear different under different conditions such as light, temperatures, fertilizer, and water, without any difference in genotype. The color descriptions used are from the 2015 edition of The Royal Horticultural Society Colour Chart except where common dictionary terms are used.

Parentage: Female or seed parent was 12-113-6, and the male or pollen parent was 18-10-5;

Plant habit: Hardy herbaceous perennial with basal rosette of foliage; mounded foliage about 24 cm tall and 46 cm in diameter with scapes to about 42 cm tall; stems to about 4 cm long and 1.5 cm diameter at base completely covered with petiole stipules, with about 16 leaves per stem and 20 main stems per plant;

Roots: Fibrous, finely branched; nearest RHS NN155B depending on soil type;

Growth rate: Vigorous, rapid; rooting from cutting in two weeks and finishing in a 3.8-liter container in about 16 weeks from a 25 mm plug;

Foliage: Cordate; shallowly penta-lobed (dissected about 15 mm deep), with basal lobes extending 35 mm beyond petiole and frequently imbricate to 5 mm; mostly flat; apex and major and minor lobe apices rounded; base cordate; margin crenate and micro-ciliolate; slightly bullate on young leaves and flat on mature leaves; adaxial micro-puberulent and abaxial surfaces sparsely puberulent, adaxial slightly lustrous becoming matte and abaxial moderately lustrous; high number of leaf indentations with four major indentations and about 40 to 60 smaller indentations; leaf margin undulation not observed;

Leaf blade size: To about 13 cm long and12.2 cm wide and, average about 10.8 cm long and 11 cm wide;

Leaf color: Seasonally variable; initial spring and expanding adaxial between veins nearest RHS 202C, surrounding veins nearest RHS N186A, initial spring and expanding abaxial between RHS N186C and RHS N186D; fully expanded adaxial leaves near flowering between the veins between RHS N189D and RHS N189C, region surrounding the veins between RHS N189A and RHS NN137A, fully expanded abaxial leaves near flowering nearest RHS N186C; late season fall adaxial region between the veins nearest RHS 189A with a slight overtone of nearest RHS 188A, region surrounding the veins between RHS N198A and RHS NN137A, late season fall abaxial nearest RHS N186C;

Veins: Palmate; micro-puberulent and slightly concave adaxial and sparsely hirsutulous and costate abaxial;

Vein color: Emerging or initial spring adaxial primary veins between RHS N170D and RHS 174D and secondary veins nearest RHS N186A, emerging or early spring abaxial primary veins nearest RHS 182C and secondary veins nearest RHS N186C; near flowering adaxial primary veins nearest RHS 177C and secondary veins between RHS N189A and RHS NN137A, near flowering season abaxial proximal midrib nearest RHS N170C, primary veins nearest RHS 187B and secondary veins nearest RHS 187A; late season fall adaxial primary veins proximally nearest RHS 146B, primary veins distally nearest RHS N148A, and secondary veins nearest RHS NN137A; late season fall abaxial primary veins proximally nearest RHS 182C, primary veins distally between RHS 182A and RHS 186A, and secondary veins nearest RHS 187A;

Petiole: Cylindrical; base amplexicaul; stiff; outer leaves outwardly and inner leaves upwardly; pubescent with hairs to about 2 mm long; to about 17 cm long, 5 mm across at base above stipule, and 3 mm across below petiole, average about 17 cm long, 4.5 mm across above stipule and 3 mm across below petiole;

Petiole color: Varying with season; young emerging between RHS 177B and RHS 197B, mid-flowering season between RHS N186C and RHS 197B, late season fall nearest RHS 197A;

Stipule: At base of petiole; adaxial and abaxial glabrous; margin ciliate; to about 17 mm long and about 14 mm wide at base and 7 mm wide at apex, with two distally-flared linear lobes about 5 mm long and 1.5 mm wide with acute apices;

Stipule color: Adaxial and abaxial variable; young expanding leaves adaxial between RHS 71D and RHS 64C, abaxial nearest RHS 186D; mature leaves adaxial nearest RHS 186D and abaxial between RHS 177D and RHS 182C;

Peduncle: Panicle; cylindrical; stiff; puberulent; upright; to about 42 cm long and 4 mm diameter at base, average about 36 cm tall and about 4 mm diameter; about 10 to 20 per plant; with about 200 flowers per panicle; with short branches;

Peduncle color: Distally nearest RHS 187A, proximally between RHS 187B and RHS 187C; branches nearest RHS 187A;

Branches: Up to 24 compound branches per peduncle; cylindrical; puberulent; to about 3.2 cm long and about 1 mm diameter at base, decreasing in size distally; aspect mostly outwardly;

Inflorescence: Flowering in upper 20 cm and 7 cm wide;

Flowering longevity: Individual panicles effective for about two weeks; producing new panicles and effective from mid-June through early fall;

Flower density: Moderately open;

Pedicel: Cylindrical; finely puberulent, to about 3 mm long and 0.5 mm diameter;

Pedicel color: Between RHS 187B and RHS 187C;

Buds one day prior to opening: Oblong ellipsoidal; acute apex and attenuate base; puberulent; about 5 mm long and 3 mm diameter near middle;

Bud color one day prior to opening: Proximal portion nearest RHS 60D, distally between RHS 60A and RHS 60B, middle portion nearest RHS 56B;

Flower: Perfect, campanulate, actinomorphic, about 8.5 mm long to exserted style and 8mm in diameter at face; calyx to 7 mm long and 8 mm diameter; corolla to 6 mm long and 6 mm diameter; individual flowers lasting about 4 days on plant or as cut flower; rarely persistent;

Flower aspect: Outwardly to slightly downwardly;

Calyx: Campanulate with base fused in proximal 4 mm to form hypanthium; about 7 mm long and 8 mm wide;

Sepals: Five; glabrous adaxial; puberulent abaxial; acute apex; fused in the basal 4 mm; rarely persistent; to 7 mm long and 2 mm across at fusion;

Calyx color: Adaxial basal portion nearest RHS NN155D, with distal portion nearest RHS 60A; abaxial proximally nearest RHS 61C, middle portion nearest RHS 65D, and distally nearest RHS 60A;

Petals: Five; spatulate; acute apex and attenuate base; margin entire; glabrous abaxial and puberulent adaxial; adnate to adaxial sepals in proximal 0.5 mm; about 3 mm long and 1 mm wide about one third of the way to apex;

Petal color: Abaxial and adaxial nearest RHS 60D;

Androecium: Five;

*Filaments*.—Five; glabrous; adnate to adaxial calyx about 1 mm above base; thin, glabrous; about 2 mm long and about 0.3 mm diameter; color nearest RHS NN155D.

*Anthers*.—Ellipsoidal, distinct, basifixed, longitudinal; about 0.5 mm long; color nearest RHS 26A.

*Pollen*.—Rare; color nearest RHS 12B.

Gynoecium: One, two-beaked; half-inferior; 6 mm long;

*Style*.—Bifid; exserted; split apart at apex of ovary; about 4 mm long and about 0.5 mm diameter; color nearest RHS NN155B.

*Stigma*.—Acute apex, about 0.5 mm diameter; color nearest RHS NN155C.

*Ovary*.—Half-inferior, about 2 mm tall and 2 mm diameter; ellipsoidal to globose; apex tapering to style, base rounded; color between RHS 145D and RHS 145C.

Fruit: Two-beaked ovoid capsule; about 7 mm long and 3 mm across; color nearest RHS 200D;

Seed: Oblong; acute apex and base; about 1 mm long and 0.5 mm across; color nearest RHS 202A;

Growth: 'Glazed and Infused' grows best with ample moisture and drainage in either sun or shade. Cold hardy from USDA zones 4 to 9.

Disease and pest tolerance: Resistance, tolerance, and susceptibility outside of that normal for *Heuchera* is not known.

It is claimed:

1. A new and distinct *Heuchera* plant named 'Glazed and Infused' as herein described and illustrated.

* * * * *